US010988425B2

(12) United States Patent
Bolomey et al.

(10) Patent No.: US 10,988,425 B2
(45) Date of Patent: Apr. 27, 2021

(54) ONE STEP PROCESS FOR MANUFACTURING TRIFLUOROIODOMETHANE FROM TRIFLUOROACETYL HALIDE, HYDROGEN, AND IODINE

(71) Applicant: Honeywell International Inc., Morris Plains, NJ (US)

(72) Inventors: Pascal Bolomey, Solon, OH (US); Terris Yang, East Amherst, NY (US); Haiyou Wang, Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/749,801

(22) Filed: Jan. 22, 2020

(65) Prior Publication Data

US 2020/0262771 A1    Aug. 20, 2020

Related U.S. Application Data

(60) Provisional application No. 62/806,989, filed on Feb. 18, 2019.

(51) Int. Cl.
*C07C 17/361* (2006.01)
*B01J 23/44* (2006.01)
*C07C 19/16* (2006.01)

(52) U.S. Cl.
CPC ............. *C07C 17/361* (2013.01); *B01J 23/44* (2013.01); *C07C 19/16* (2013.01)

(58) Field of Classification Search
CPC ........ C07C 17/093; C07C 17/361; C07C 19/16
See application file for complete search history.

(56) References Cited

U.S. PATENT DOCUMENTS

| 4,410,505 | A | * | 10/1983 | O'Keefe | ................... | C01B 3/06 423/501 |
| 6,946,582 | B2 | | 9/2005 | Katsube et al. | | |
| 6,977,316 | B1 | | 12/2005 | Mukhopadhyay et al. | | |
| 2006/0122440 | A1 | * | 6/2006 | Mukhopadhyay | .... | C07C 17/093 570/152 |
| 2007/0106092 | A1 | | 5/2007 | Picozzi et al. | | |

FOREIGN PATENT DOCUMENTS

| WO | 2006/063241 A2 | 6/2006 |
| WO | 2006/086057 A2 | 8/2006 |

OTHER PUBLICATIONS

International Search Report and Written Opinion received for PCT Patent Application No. PCT/US2020/017888, dated Jun. 9, 2020, 11 pages.

* cited by examiner

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane ($CF_3I$). The process includes providing vapor-phase reactants including trifluoroacetyl halide, hydrogen, and iodine, heating the vapor-phase reactants, and reacting the heated vapor-phase reactants in the presence of a catalyst to produce trifluoroiodomethane. The catalyst includes a transition metal.

20 Claims, 1 Drawing Sheet

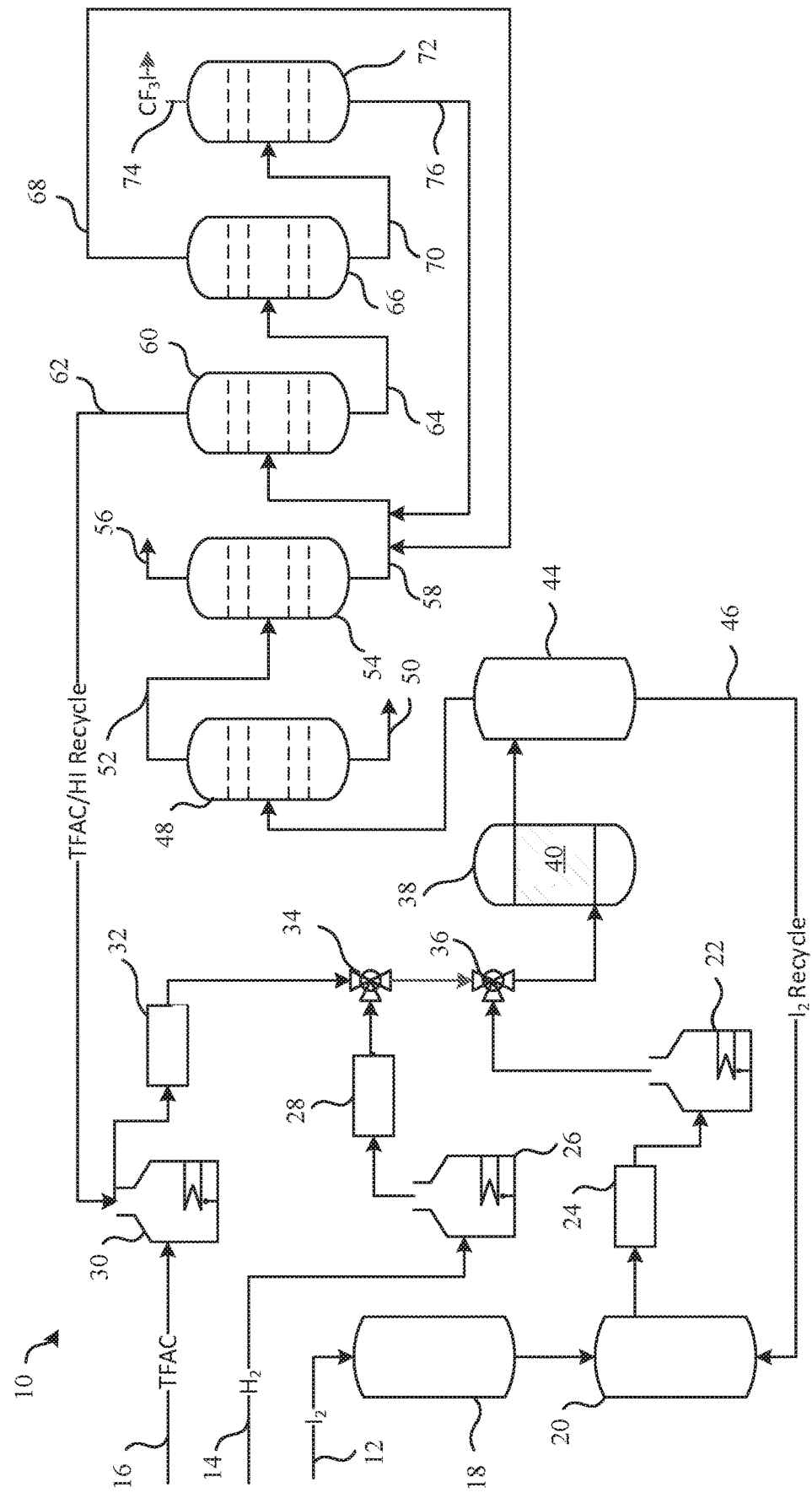

ONE STEP PROCESS FOR MANUFACTURING TRIFLUOROIODOMETHANE FROM TRIFLUOROACETYL HALIDE, HYDROGEN, AND IODINE

CROSS-REFERENCE TO RELATED APPLICATION

This application claims priority to U.S. Provisional Application No. 62/806,989, filed Feb. 18, 2019, which is herein incorporated by reference in its entirety.

FIELD

The present disclosure relates to processes for producing trifluoroiodomethane ($CF_3I$). Specifically, the present disclosure relates to catalysts and integrated processes to produce trifluoroiodomethane.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and a low ozone depletion potential. Trifluoroiodomethane can replace more environmentally damaging materials.

Methods of preparing trifluoroiodomethane are known. For example, U.S. Pat. No. 7,132,578 (Mukhopadhyay et al.) discloses a catalytic, one-step process for producing trifluoroiodomethane from trifluoroacetyl chloride. However, the source of iodine, is iodine fluoride (IF). Iodine fluoride is relatively unstable, decomposing above 0° C. to $I_2$ and $IF_5$. Iodine fluoride may also not be available in commercially useful quantities.

In another example, U.S. Pat. No. 7,196,236 (Mukhopadhyay et al.) discloses a catalytic process for producing trifluoroiodomethane using reactants comprising a source of iodine, such as hydrogen iodide, at least a stoichiometric amount of oxygen, and a reactant $CF_3R$, where R is selected from the group consisting of —COOH, —COX, —CHO, —$COOR_2$, AND —$SO_2X$, where $R_2$ is alkyl group and X is a chlorine, bromine, or iodine. Hydrogen iodide, which may be produced by the reaction, is oxidized by the at least a stoichiometric amount of oxygen, producing water and iodine for economic recycling.

Several other processes are referenced in the literature for making $CF_3I$ from trifluoroacetyl chloride with hydrogen iodide in a vapor phase reaction. However, the production of $CF_3I$ from trifluoroacetyl chloride and hydrogen iodide requires an extra step to make hydrogen iodide. The present disclosure introduces a one-step process to make $CF_3I$ by co-feeding trifluoroacetyl halide, hydrogen and iodine into a reactor with the presence of a catalyst.

SUMMARY

The present disclosure provides processes for producing trifluoroiodomethane from hydrogen ($H_2$), elemental iodine ($I_2$), and a trifluoroacetyl halide ($CF_3C(O)X$).

In one embodiment, the present invention provides a process for producing trifluoroiodomethane ($CF_3I$). The process includes providing vapor-phase reactants including trifluoroacetyl halide, hydrogen, and iodine, heating the vapor-phase reactants, and reacting the heated vapor-phase reactants in the presence of a catalyst to produce trifluoroiodomethane. The catalyst includes a transition metal.

In another embodiment, the present invention provides a process for producing trifluoroiodomethane ($CF_3I$). The process includes the steps of reacting a trifluoroacetyl halide, hydrogen, and iodine in the vapor phase at a temperature from about 200° C. to about 600° C. in the presence of a catalyst to produce a product stream comprising the trifluoroiodomethane, unreacted trifluoroacetyl halide, unreacted hydrogen, unreacted iodine, hydrogen halide, and hydrogen iodide. The catalyst includes a transition metal. The process further includes removing at least some of the unreacted iodine from the product stream by cooling the product stream to condense iodine from the vapor phase and recycling the condensed iodine to the reacting step.

The above mentioned and other features of the disclosure, and the manner of attaining them, will become more apparent and will be better understood by reference to the following description of embodiments.

BRIEF DESCRIPTION OF THE DRAWINGS

The FIGURE is a process flow diagram showing an integrated process for manufacturing trifluoroiodomethane.

DETAILED DESCRIPTION

The present disclosure provides a one-step process for the manufacture of trifluoroiodomethane ($CF_3I$) from trifluoroacetyl halide ($CF_3C(O)X$), hydrogen ($H_2$), and iodine ($I_2$) that includes the use of a transition metal catalyst. It has been found that reacting at about 200° C. to about 600° C. in the presence of the transition metal catalyst provides for the efficient manufacture of trifluoroiodomethane from these readily available reactants. Efficiency is further enhanced by the recycling the reactants.

As disclosed herein, the trifluoroiodomethane is produced in a one-step process in which the reactants trifluoroacetyl halide, hydrogen ($H_2$) and iodine ($I_2$) are co-fed into a reactor in the presence of a catalyst at reaction temperature of about 200° C. to about 600° C. All reactants are anhydrous. It is preferred that there be as little water in the reactants as possible because any water in the reaction may favor secondary reaction pathways resulting in the formation of undesired byproducts, such as trifluoromethane ($CF_3H$).

The trifluoroacetyl halide is substantially free of water. That is, any water in the trifluoroacetyl halide is in an amount by weight less than about 500 parts per million (ppm), about 300 ppm, about 200 ppm, about 100 ppm, about 50 ppm, about 30 ppm, about 20 ppm, or about 10 ppm, or less than any value defined between any two of the foregoing values. Preferably, any water in the trifluoroacetyl halide is in an amount by weight less than about 100 ppm. More preferably, any water in the trifluoroacetyl halide is in an amount by weight less than about 30 ppm. Most preferably, any water in the trifluoroacetyl halide is in an amount by weight less than about 10 ppm.

The iodine is substantially free of water. That is, any water in the iodine is in an amount by weight less than about 500 ppm, about 300 ppm, about 200 ppm, about 100 ppm, about 50 ppm, about 30 ppm, about 20 ppm, or about 10 ppm, or less than any value defined between any two of the foregoing values. Preferably, any water in the iodine is in an amount by weight less than about 100 ppm. More preferably, any water in the iodine is in an amount by weight less than about 30 ppm. Most preferably, any water in the iodine is in an amount by weight less than about 10 ppm.

The hydrogen is substantially free of water. That is, any water in the hydrogen is in an amount by weight less than about 500 ppm, about 300 ppm, about 200 ppm, about 100 ppm, about 50 ppm, about 30 ppm, about 20 ppm, or about 10 ppm, or less than any value defined between any two of the foregoing values. Preferably, any water in the hydrogen is in an amount by weight less than about 100 ppm. More preferably, any water in the hydrogen is in an amount by weight less than about 30 ppm. Most preferably, any water in the hydrogen is in an amount by weight less than about 10 ppm.

The trifluoroacetyl halide is selected from the group consisting of trifluoroacetyl fluoride ($CF_3C(O)F$), trifluoroacetyl chloride ($CF_3C(O)Cl$), trifluoroacetyl bromide ($CF_3C(O)Br$), and any combinations thereof. Preferably, the trifluoroacetyl halide comprises trifluoroacetyl chloride. More preferable, the trifluoroacetyl halide consists essentially of trifluoroacetyl chloride. Most preferably, the trifluoroacetyl halide consists of trifluoroacetyl chloride.

Trifluoroacetyl chloride, for example, is readily available in commercial quantities from Halocarbon Products Corporation, Peachtree Corners, Ga., or from Solvay S. A., Brussels, Belgium, for example. Hydrogen is commercially available from Air Products, Allentown, Pa. Solid iodine is commercially available from SQM, Santiago, Chile, or Kanto Natural Gas Development Co., Ltd, Chiba, Japan.

The reactants may be provided for the reaction at a mole ratio of hydrogen to iodine as low as about 0.1:1, about 0.2:1, about 0.3:1, about 0.4:1, about 0.5:1, about 0.6:1, about 0.7:1, about 0.8:1, about 0.9:1, or about 1:1, or as high as 1.1:1, 1.2:1, 1.5:1, 2:1, 2.5:1, 3:1, 4:1, or 5:1, or within any range defined between any two of the foregoing values, such as about 0.1:1 to about 5:1, about 0.2:1 to about 4:1, about 0.3:1 to about 3:1, about 0.4:1 to about 2.5:1, about 0.5:1 to about 2:1, about 0.5:1 to about 1.5:1, about 0.7:1 to about 1.2:1, about 0.8:1 to about 1.1:1, or about 0.9:1 to about 1:1, for example. Preferably, the mole ratio of hydrogen to iodine is from about 0.1:1 to about 1:1. More preferably, the mole ratio of hydrogen to iodine is from about 0.3:1 to about 0.8:1. Most preferably, the mole ratio of hydrogen to iodine is from about 0.5:1 to about 0.7:1. It has been found that a mole ratio of hydrogen to iodine less than 1 provides significantly better yields than ratios greater than 1. Without wishing to be bound by any theories, it is believed that with a mole ratio of hydrogen to iodine less than 1, little hydrogen is available for competing side reactions that form undesired byproducts from the trifluoroacetyl halide, such as $CF_3H$ and $CH_3I$.

The reactants may be provided for the reaction at a mole ratio of hydrogen to trifluoroacetyl halide as low as about 0.002:1, about 0.004:1, about 0.006:1, about 0.008:1, about 0.01:1, about 0.02:1, about 0.03:1, about 0.04:1, or as high as about 0.05:1, about 0.07:1, about 0.09:1, about 0.1:1, about 0.2:1, about 0.3:1, about 0.4:1, about 0.5:1, or about 1:1, or within any range defined between any two of the foregoing values, such as about 0.002:1 to about 1:1, about 0.004:1 to about 0.5:1, about 0.006:1 to about 0.4:1, or about 0.01:1 to 0.1:1, for example. Preferably, the mole ratio of hydrogen to trifluoroacetyl halide is from about 0.01:1 to about 0.05:1.

The reactants react in the presence of a catalyst contained within a reactor to produce a product stream comprising trifluoroiodomethane and reaction by-products carbon monoxide (CO) and hydrogen halide (HX) according to Equation 1 below:

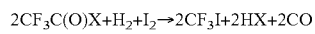
$$2CF_3C(O)X+H_2+I_2 \rightarrow 2CF_3I+2HX+2CO \qquad \text{Eq. 1:}$$

wherein X is fluoride, chloride, or bromide, depending on the trifluoroacetyl halide reactant chosen. Thus, the hydrogen halide is hydrogen fluoride (HF), hydrogen chloride (HCl), and/or hydrogen fluoride (HBr).

It is believed that within the reactor, the hydrogen and iodine react to form hydrogen iodide (HI) in situ, which then almost immediately reacts with the trifluoroacetyl halide to form trifluoroiodomethane. Competing side reactions may produce some byproducts such as trifluoromethane ($CF_3H$), iodomethane ($CH_3I$), and trifluoroacetyl iodide (TFAI), for example. The reactor may be a heated tube reactor, such as fixed bed tubular reactor, including a tube containing the catalyst. The tube may be made of a metal such as stainless steel, nickel, and/or a nickel alloy, such as a nickel-molybdenum alloy, a nickel-chromium-molybdenum alloy, or a nickel-copper alloy. The tube reactor is heated, thus also heating the catalyst. Alternatively, the reactor may be any type of packed reactor.

The reaction is carried out substantially free of oxygen ($O_2$). That is, any oxygen during the reaction is, by weight, less than about 500 parts per million, about 300 ppm, about 200 ppm, about 100 ppm, about 50 ppm, about 30 ppm, about 20 ppm, about 10 ppm, about 5 ppm, about 3 ppm, about 2 ppm, or about 1 ppm, or less than any value defined between any two of the foregoing values. Preferably, any oxygen during the reaction is less than about 100 ppm. More preferably, any oxygen during the reaction is less than about 10 ppm. Most preferably, any oxygen during the reaction is less than about 3 ppm. It is preferred that there be as little oxygen as possible during the reaction because it may oxidize at least some of the hydrogen iodide to form iodine and water before the hydrogen iodide can react to form trifluoroiodomethane, thereby reducing the efficiency of the process.

The catalyst includes a transition metal. Preferably, the transition metal includes non-precious transition metals nickel, cobalt, or iron, or precious transition metals rhodium, iridium, platinum, palladium, or any combination thereof. More preferably, the transition metal consists essentially of nickel, platinum, palladium, or combinations thereof. Most preferably, the transition metal consists essentially of palladium.

The catalyst may include a support for the transition metal. Preferably, the support includes carbon, aluminum oxide ($Al_2O_3$), silica gel ($SiO_2$), silicon carbide (SiC), or combinations thereof. Most preferably, the support consists essentially of aluminum oxide.

The amount of transition metal on the surface of the catalyst, as a percentage of the total combined weight of the transition metal and the support may be as little as about 0.01 weight percent (wt. %), about 0.02 wt. %, about 0.1 wt. %, about 0.3 wt. %, about 0.5 wt. %, about 0.7 wt. %, about 1 wt. %, about 2 wt. %, or about 4 wt. % or as great as about 6 wt. %, about 8 wt. %, about 10 wt. %, about 15 wt. %, about 20 wt. %, about 21 wt. %, about 25 wt. %, about 30 wt. %, or about 40 wt. %, or within any range defined between any two of the foregoing values, such as about 0.01 wt. % to about 40 wt. %, about 0.02 wt. % to about 30 wt. %, about 0.1 wt. % to about 25 wt. %, about 0.3 wt. % to about 20 wt. %, about 0.5 wt. % to about 15 wt. %, about 0.7 wt. % to about 10 wt. %, about 1 wt. % to about 8 wt. %, about 2 wt. % to about 6 wt. %, about 1 wt. % to about 4 wt. %, or about 0.3 wt. % to about 0.7 wt. %, for example. Preferably, the amount of non-precious transition metal on the surface of the catalyst is from about 5 wt. % to about 35 wt. %. More preferably, the amount of non-precious transition metal on the surface of the catalyst is from about 10 wt.

% to about 30 wt. %. Most preferably, amount of non-precious transition metal on the surface of the catalyst is from about 20 wt. % to about 30 wt. %. Preferably, the amount of precious transition metal on the surface of the catalyst is from about 0.1 wt. % to about 5 wt. %. More preferably, the amount of precious transition metal on the surface of the catalyst is from about 0.3 wt. % to about 1 wt. %. Most preferably, amount of precious transition metal on the surface of the catalyst is from about 0.3 wt. % to about 0.7 wt. %.

The reactants may be in contact with the catalyst for a contact time as short as about 0.1 second, 1 second, about 2 seconds, about 4 seconds, about 6 seconds, about 8 seconds, about 10 seconds, about 15 seconds, about 20 seconds, about 25 seconds, or about 30 seconds, or as long as about 40 seconds, about 50 seconds, about 60 seconds, about 70 seconds, about 80 seconds, about 100 seconds about 120 seconds, or about 1,200 seconds, or within any range defined between any two of the foregoing values, such as about 0.1 second to about 1,200 seconds, about 2 seconds to about 120 seconds, about 4 second to about 100 seconds, about 6 seconds to about 80 seconds, about 8 seconds to about 70 seconds, about 10 seconds to about 60 seconds, about 15 seconds to about 50 seconds, about 20 seconds to about 40 seconds, about 20 seconds to about 30 seconds, about 10 seconds to about 20 seconds, or about 100 seconds to about 120 seconds, for example. Preferably, the reactants are in contact with the catalyst for a contact time from about 1 second to about 100 seconds. More preferably, the reactants are in contact with the catalyst for a contact time from about 2 seconds to about 50 seconds. Most preferably, the reactants are in contact with the catalyst for a contact time from about 10 seconds to about 30 seconds.

The reaction is conducted at a temperature as low as about 200° C., about 250° C., about 300° C., about 320° C., about 330° C., about 340° C., about 350° C., or to a temperature as high as about 360° C., about 370° C., about 380° C., about 390° C., about 400° C., 500° C., or about 600° C., or within any range defined between any two of the foregoing values, such as about 200° C. to about 600° C., about 250° C. to about 500° C., about 300° C. to about 400° C., about 320° C. to about 390° C., about 340° C. to about 380° C., about 350° C. to about 370° C., or about 340° C. to about 360° C., for example. Preferably, the reactants are heated to a temperature from about 300° C. to about 400° C. More preferably, the reactants are heated to a temperature from about 320° C. to about 360° C. Most preferably, the reactants are heated to a temperature from about 340° C. to about 360° C.

Pressure is not critical. Convenient operating pressures range from about 10 kPa to about 4,000 kPa, and preferably from about 100 kPa to about 350 kPa.

The composition of the organic compounds in the product stream exiting the reactor may be measured by gas chromatography (GC) and gas chromatography-mass spectroscopy (GC-MS) analyses. Graph areas provided by the GC analysis for each of the organic compounds may be combined to provide a GC area percentage (GC area %) of the total organic compounds for each of the organic compounds as a measurement of the relative concentrations of the organic compounds in the product stream.

The concentration of trifluoroiodomethane in the product stream exiting the reactor, in GC area % of total organic compounds not including the trifluoroacetyl halide, may be as low as about 10%, about 15%, about 20%, about 25%, about 30%, about 35%, about 40%, about 45%, about 50%, about 55% or about 60%, or may be as high as about 65%, about 70%, about 75%, about 80%, about 85%, about 90%, about 95%, about or 99% or within any range defined between any two of the foregoing values, such as about 10% to about 99%, about 20% to about 95%, about 30% to about 90%, about 40% to about 85%, about 45% to about 80%, about 50% to about 75%, about 55% to about 70%, about 60% to about 65%, about 90% to about 99% or about 95% to about 99%, for example. Preferably, the concentration of trifluoroiodomethane in the product stream is from about 30% to about 99%. More preferably, the concentration of trifluoroiodomethane in the product stream is from about 70% to about 99%. Most preferably, the concentration of trifluoroiodomethane in the product stream is from about 90% to about 99%.

The product stream is directed from the reactor to one or more iodine removal vessels in which the product stream is cooled to allow unreacted iodine to condense to remove at least some of the iodine from the product stream to be recycled as a reactant. The product stream may be cooled to a temperature lower than the boiling point of iodine, but above the melting point of iodine, to condense the iodine in liquid form. Alternatively, or additionally, the product stream leaving the reactor may be cooled to a temperature lower than the melting point of iodine to recover the iodine in solid form. The product stream may proceed from the iodine removal vessel to one or more additional iodine removal vessels to remove additional unreacted iodine for recycle.

The product stream may be directed from the one or more iodine removal vessels to a heavies distillation column to separate higher boiling point byproducts, such as methyl iodide ($CH_3I$) and trifluoroacetyl iodide (TFAI), from the trifluoroiodimethane ($CF_3I$), unreacted trifluoroacetyl halide ($CF_3C(O)X$), and other byproducts such as trifluoromethane ($CF_3H$), hydrohalic acid (HX), hydrogen iodide (HI), and carbon monoxide (CO). An overhead stream from the heavies distillation column including the $CF_3I$, $CF_3C(O)X$, $CF_3H$, HX, HI, $H_2$ and CO may be directed to a lights distillation column to separate the higher boiling compounds, such as $CF_3C(O)X$, HI, and $CF_3I$, from the lower boiling compounds such as $CF_3H$, HX, CO, and $H_2$. An overhead stream from the lights distillation column including $CF_3H$, HX, CO, and $H_2$ may be directed to a scrubber to remove the HX, and then to a thermal oxidizer. The higher boiling point compounds $CF_3C(O)X$, HI, and $CF_3I$ may be directed from a bottom stream of the lights distillation column to one or more distillation columns to separate the $CF_3C(O)X$ and HI from the $CF_3I$. The separated $CF_3C(O)X$ and HI may be recycled back to the reactor. The separated $CF_3I$ may be directed to one or more product distillation columns to separate the $CF_3I$ product. The $CF_3I$ may be collected from the overhead stream of the last product distillation column. The recycle of the iodine, the $CF_3C(O)X$, and the HI results in an efficient process for producing $CF_3I$.

The FIGURE is a process flow diagram showing an integrated process 10 for manufacturing trifluoroiodomethane. As shown in the FIGURE, the process 10 includes material flows of solid iodine 12, hydrogen 14, and a trifluoroacetyl halide, trifluoroacetyl chloride (TFAC) 16. The solid iodine 12 may be continuously or intermittently added to a solid storage tank 18. A constant flow of solid iodine is transferred by a solid conveying system (not shown) from the solid storage tank 18 to an iodine liquefier 20 where the solid iodine is heated to above its melting point but below its boiling point to maintain a level of liquid iodine in the iodine liquefier 20. Liquid iodine flows from the iodine liquefier 20 to an iodine vaporizer 22. The iodine liquefier 20 may be pressurized by an inert gas to drive the flow of liquid iodine. The inert gas may include nitrogen, argon, or helium, or mixtures thereof, for example. The flow rate of the liquid iodine may be controlled by a liquid flow controller 24. In the iodine vaporizer 22, the iodine is heated to above its boiling point to form a flow of iodine vapor.

The hydrogen 14 may be provided to a hydrogen preheater 26, where the hydrogen 14 is heated to a selected reaction temperature. The flow rate of the heated hydrogen may be controlled by a gas flow controller 28.

The TFAC 16 may be provided to a TFAC preheater 30, where the TFAC is heated to a selected reaction temperature. The flow rate of the heated TFAC may be controlled by a gas flow controller 32. The flow of heated hydrogen and the flow of heated TFAC may be combined in a mixing valve 34, which may then be combined with the flow of iodine vapor in another mixing valve 36. Alternatively, the flow of heated hydrogen, the flow of heated TFAC, and the flow of iodine may be combined in a single mixing valve. The heated mixture of iodine vapor, hydrogen and TFAC is provided to a reactor 38.

The heated mixture of iodine vapor, hydrogen and TFAC reacts in the presence of a catalyst 40 contained within the reactor 38 to produce a crude product stream. The catalyst 40 is any of the catalysts described herein. The crude product stream may include trifluoroiodomethane, unreacted hydrogen, unreacted iodine, unreacted TFAC, and reaction by-products such as HI, CO, $CF_3H$, TFAI, HCl, and $CH_3I$, for example.

The crude product stream is provided to an iodine removal vessel 44. The crude product stream is cooled in the iodine removal vessel 44 to a temperature below the boiling point of the iodine to condense at least some of the iodine, separating it from the crude product stream. The iodine collected in the iodine removal vessel 44 forms an iodine recycle stream 46. The iodine recycle stream 46 is provided to the iodine liquefier 20 to recycle the iodine.

The crude product stream may be further cooled in the iodine removal vessel 44 to a temperature below the melting point of the iodine to separate even more iodine from the crude product stream, depositing at least some of the iodine within the iodine removal vessel 44 as a solid. The iodine removal vessel 44 may subsequently be taken offline and the solid iodine heated to liquefy the iodine for the iodine recycle stream 46.

Although a single iodine removal vessel 44 is shown, it is understood that the iodine removal vessel 44 may include two or more iodine removal vessels 44 operating in a parallel configuration, two or more iodine removal vessels 44 operating in a series configuration, and any combination thereof. It is also understood that the iodine removal vessel 44 may include multiple trains of iodine removal vessels 44, such that at least one train is in operation while another train is offline for removal of solid iodine in order to provide continuous operation while collecting the iodine in solid form.

The crude product stream is provided from the iodine removal vessel 44 to a heavies distillation column 48. The heavies distillation column 48 is configured for the separation of organic heavies, such as $CH_3I$ and TFAI, from organic lights, such as $CF_3I$, unreacted TFAC, and byproducts such as HI, CO, $CF_3H$, and HCl. A bottom stream 50 including the organic heavies from the heavies distillation column 48 may be provided to a vessel (not shown). The organic heavies in the vessel may be disposed of, or may be further distilled to recover the components for further use or sale.

An overhead stream 52 including the organic lights from the heavies distillation column 48 including $CF_3I$, TFAC, $CF_3H$, HCl, HI, $H_2$ and CO is directed to a lights distillation column 54 to separate the higher boiling compounds, such as TFAC, HI, and $CF_3I$, from the lower boiling compounds such as $CF_3H$, HCl, CO, and $H_2$. An overhead stream 56 of the lights distillation column 54 including $CF_3H$, HCl, CO, and $H_2$ may be provided to scrubber (not shown) for removal of the HCl, and then provided to a thermal oxidizer (not shown) for oxidation of the $CF_3H$, CO, and $H_2$.

A bottom stream 58 including the $CF_3I$, TFAC, and HI from the lights distillation column 54 is provided to a recycle column 60. The recycle column 60 is configured to separate the $CF_3I$ from the TFAC and HI. An overhead stream 62 of the recycle column 60 including the TFAC and HI forms a TFAC/HI recycle stream. The TFAC/HI recycle stream 62 is provided to the TFAC preheater 30 to recycle the TFAC and the HI. Although a single recycle column 60 is shown, it is understood that the recycle column 60 may include two or more recycle columns operating in series, parallel, or any combination thereof to achieve a desired separation efficiency.

A bottom stream 64 including the $CF_3I$ and trace amounts of organic lights and heavies from the recycle column 60 is provided to a first product column 66. The first product column 66 is configured to separate the $CF_3I$ from the trace amount of organic lights. An overhead stream 68 of the first product column 66 including the organic lights and some $CF_3I$ may be recycled to bottom stream 58 provided to the recycle column 60 to recover additional $CF_3I$. A bottom stream 70 including $CF_3I$ and the organic heavies from the first product column 66 is provided to a second product column 72. The product $CF_3I$ is collected from an overhead stream 74 of the second product column 72. A bottom stream 76 including some $CF_3I$ and organic heavies from the second product column 72 may be recycled to the bottom stream 58 provided to the recycle column 60 to recover additional $CF_3I$.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Examples 1-4: Production of $CF_3I$ from Trifluoroacetyl Chloride (TFAC), Hydrogen, and Elemental Iodine In the following Examples, the manufacture of trifluoroiodomethane from TFAC, hydrogen and iodine according to Equation 1 described above is demonstrated. A three-quarter inch Inconel 600 tube 11.5 inches in length was used as a reactor and charged with 11 inches of either 0.1 wt. % $Pd/Al_2O_3$ catalyst from Johnson Matthey or 0.5 wt. % $Pd/Al_2O_3$ catalyst from BASF. The reactor was preheated to 350° C. A certain amount of TFAC and $H_2$ was co-fed into a TFAC/$H_2$ preheater, as shown in the Table below, and then fed into an $I_2$ vaporizer which was initially charged with 1000 grams of solid iodine. The $I_2$ vaporizer temperature was controlled at 150-165° C., which generated $I_2$ vapor. The mixture of $I_2$ vapor, TFAC vapor and $H_2$ vapor was then fed into the heated fixed bed tubular reactor which was loaded with the catalyst. The reactor effluent was passed through a two-stage $I_2$ collector to capture any unreacted $I_2$ in a solid form, and then fed into a de-ionized water scrubber to capture un-reacted TFAC, as well as HCl and HI generated during the reaction.

Periodically, samples were taken from the effluent of the deionized water scrubber, and the composition of the organic compounds in the samples were measured by gas chromatography (GC). Graph areas provided by the GC analysis for each of the organic compounds were combined to provide a GC area percentage (GC area %) of the total organic compounds.

At the end of the run time of the reaction, the system was shut down and the weight loss of the iodine vaporizer and the weight gain of the iodine removal vessels were measured to determine a feed rate of iodine. The feed rate of iodine was compared to the feed rate of hydrogen to determine an average molar ratio of $H_2$:$I_2$ fed to the reactor. A residence time in the reactor was calculated based on the combined feed rates of the hydrogen, the iodine, and the TFAC.

The results for each Example are shown in Table 1. For each Example, Table 1 shows the amount of palladium on aluminum oxide catalyst used, the feed rate of TFAC, the feed rate of $H_2$, the average molar feed ratio of $H_2$ to $I_2$, the average molar feed ratio of TFAC to HI, the residence time, and the GC area % for $CF_3I$, $CF_3H$, and $CH_3I$ at the end of the run. Examples 1, 3 and 4 were run for 24 hours and Example 2 was run for 20 hours. As shown in Table 1, Examples with an average molar feed ratio of $H_2$ to $I_2$ less than 1:1 and with an average molar feed ratio of $H_2$ to TFAC less than 0.05:1 produced substantially better selectivity for $CF_3I$. It also appears that a larger amount of palladium on the support improves selectivity for $CF_3I$ when the average molar feed ratio of $H_2$ to $I_2$ is less than 1:1 and the average molar feed ratio of $H_2$ to TFAC is less than 0.05:1.

Aspect 3 is the process of Aspect 1, wherein the trifluoroacetyl halide comprises less than about 100 ppm by weight of water.

Aspect 4 is the process of Aspect 1, wherein the trifluoroacetyl halide comprises less than about 30 ppm by weight of water.

Aspect 5 is the process Aspect 1, wherein the trifluoroacetyl halide comprises less than about 10 ppm by weight of water.

Aspect 6 is the process of any of Aspects 1-5, wherein the hydrogen comprises less than about 500 ppm by weight of water.

Aspect 7 is the process of any of Aspects 1-5, wherein the hydrogen comprises less than about 100 ppm by weight of water.

Aspect 8 is the process of any of Aspects 1-5, wherein the hydrogen comprises less than about 30 ppm by weight of water.

Aspect 9 is the process of any of Aspects 1-5, wherein the hydrogen comprises less than about 10 ppm by weight of water.

Aspect 10 is the process of any of Aspects 1-9, wherein the iodine comprises less than about 500 ppm by weight of water.

Aspect 11 is the process of any of Aspects 1-9, wherein the iodine comprises less than about 100 ppm by weight of water.

Aspect 12 is the process of any of Aspects 1-9, wherein the iodine comprises less than about 30 ppm by weight of water.

Aspect 13 is the process of any of Aspects 1-9, wherein the iodine comprises less than about 10 ppm by weight of water.

Aspect 14 is the process of any of Aspects 1-13, wherein in the providing step, a molar ratio of the hydrogen to the iodine is from about 0.1:1 to about 5:1.

Aspect 15 is the process of any of Aspects 1-13, wherein in the providing step, a molar ratio of the hydrogen to the iodine is from about 0.1:1 to about 1:1.

Aspect 16 is the process of any of Aspects 1-13, wherein in the providing step, a molar ratio of the hydrogen to the iodine is from about 0.3:1 to about 0.8:1.

TABLE 1

| Ex. # | Pd/Al$_2$O$_3$ (Wt. %) | Feed rate TFAC (g/h) | Feed rate H$_2$ (mL/min) | H$_2$:I$_2$ | H$_2$:TFAC | Residence time (sec) | CF$_3$I (GC area %) | CF$_3$H (GC area %) | CH$_3$I (GC area %) |
|---|---|---|---|---|---|---|---|---|---|
| 1 | 0.1 | 13.4 | 20 | 0.53:1 | 0.02:1 | 15.4 | 77.5 | 4.5 | 0.3 |
| 2 | 0.1 | 7.0 | 40 | 1.18:1 | 0.09:1 | 16.0 | 49.7 | 21.3 | 14.7 |
| 3 | 0.5 | 7.5 | 40 | 1.16:1 | 0.07:1 | 15.7 | 38.4 | 17.1 | 38.7 |
| 4 | 0.5 | 13.4 | 20 | 0.62:1 | 0.02:1 | 16.3 | 94.9 | 0.5 | 1.1 |

ASPECTS

Aspect 1 is a process for producing trifluoroiodomethane ($CF_3I$), the process including providing vapor-phase reactants comprising trifluoroacetyl halide, hydrogen, and iodine; heating the vapor-phase reactants; and reacting the heated vapor-phase reactants in the presence of a catalyst to produce trifluoroiodomethane, the catalyst comprising a transition metal.

Aspect 2 is the process of Aspect 1, wherein the trifluoroacetyl halide comprises less than about 500 ppm by weight of water.

Aspect 17 is the process of any of Aspects 1-13, wherein in the providing step, a molar ratio of the hydrogen to the iodine is from about 0.5:1 to about 0.7:1.

Aspect 18 is the process of any of Aspects 1-17, wherein in the providing step, a molar ratio of the hydrogen to trifluoroacetyl halide is from about 0.002:1 to about 1:1.

Aspect 19 is the process of any of Aspects 1-17, wherein in the providing step, a molar ratio of the hydrogen to trifluoroacetyl halide is from about 0.01:1 to about 0.05:1.

Aspect 20 is the process of any of Aspects 1-19, wherein in the providing step, the vapor-phase reactants comprise less than about 500 ppm by weight of oxygen.

Aspect 21 is the process of any of Aspects 1-19, wherein in the providing step, the vapor-phase reactants comprise less than about 100 ppm by weight of oxygen.

Aspect 22 is the process of any of Aspects 1-19, wherein in the providing step, the vapor-phase reactants comprise less than about 10 ppm by weight of oxygen.

Aspect 23 is the process of any of Aspects 1-19, wherein in the providing step, the vapor-phase reactants comprise less than about 3 ppm by weight of oxygen.

Aspect 24 is the process of any of Aspects 1-23, wherein the transition metal includes at least one selected from the group of nickel, cobalt, iron, rhodium, iridium, platinum, and palladium.

Aspect 25 is the process of any of Aspects 1-23, wherein the transition metal consists essentially of nickel, platinum, palladium, or combinations thereof.

Aspect 26 is the process of any of Aspects 1-23, wherein the transition metal consists essentially of nickel, platinum, palladium, or combinations thereof.

Aspect 27 is the process of any of Aspects 1-23, wherein the transition metal consists essentially of palladium.

Aspect 28 is the process of any of Aspects 1-27, wherein the catalyst further comprises a support including at least one selected from the group of an aluminum oxide support, a carbon support, a silica gel support, and a silicon carbide support.

Aspect 29 is the process of any of Aspects 1-27, wherein the catalyst further comprises a support consisting essentially of an aluminum oxide support.

Aspect 30 is the process of either of Aspects 28 or 29, wherein an amount of transition metal on the surface of the catalyst is from about 0.01 wt. % to about 40 wt. % of the total weight of the transition metal and the support.

Aspect 31 is the process of Aspect 30, wherein the transition metal includes at least one selected from the group of nickel, cobalt, iron, or combinations thereof, and the amount of transition metal on the surface of the catalyst is from about 5 wt. % to about 35 wt. % of the total weight of the transition metal and the support.

Aspect 32 is the process of Aspect 30, wherein the transition metal includes at least one selected from the group of nickel, cobalt, iron, or combinations thereof, and the amount of transition metal on the surface of the catalyst is from about 10 wt. % to about 30 wt. % of the total weight of the transition metal and the support.

Aspect 33 is the process of Aspect 30, wherein the transition metal includes at least one selected from the group of nickel, cobalt, iron, or combinations thereof, and the amount of transition metal on the surface of the catalyst is from about 20 wt. % to about 30 wt. % of the total weight of the transition metal and the support.

Aspect 34 is the process of Aspect 30, wherein the transition metal includes nickel, the support includes aluminum oxide, and the nickel is about 21 wt. % the total weight of the nickel and the aluminum oxide.

Aspect 35 is the process of Aspect 30, wherein the transition metal includes at least one selected from the group of rhodium, iridium, platinum, palladium, or combinations thereof, and the amount of transition metal on the surface of the catalyst is from about 0.1 wt. % to about 5 wt. % of the total weight of the transition metal and the support.

Aspect 36 is the process of Aspect 30, wherein the transition metal includes at least one selected from the group of rhodium, iridium, platinum, palladium, or combinations thereof, and the amount of transition metal on the surface of the catalyst is from about 0.3 wt. % to about 1 wt. % of the total weight of the transition metal and the support.

Aspect 37 is the process of Aspect 30, wherein the transition metal includes at least one selected from the group of rhodium, iridium, platinum, palladium, or combinations thereof, and the amount of transition metal on the surface of the catalyst is from about 0.3 wt. % to about 0.7 wt. % of the total weight of the transition metal and the support.

Aspect 38 is the process of Aspect 30, wherein the transition metal includes palladium, the support includes aluminum oxide, and the palladium is about 0.5 wt. % the total weight of the palladium and the aluminum oxide.

Aspect 39 is the process of any of Aspects 1-38, wherein the vapor-phase reactants are heated to a temperature from about 200° C. to about 600° C.

Aspect 40 is the process of any of Aspects 1-38, wherein the vapor-phase reactants are heated to a temperature from about 300° C. to about 400° C.

Aspect 41 is the process of any of Aspects 1-38, wherein the vapor-phase reactants are heated to a temperature from about 320° C. to about 360° C.

Aspect 42 is the process of any of Aspects 1-38, wherein the vapor-phase reactants are heated to a temperature from about 340° C. to about 360° C.

Aspect 43 is the process of any of Aspects 1-42, wherein in the reacting step, a contact time of the vapor-phase reactants with the catalyst is from about 0.1 second to about 1,200 seconds.

Aspect 44 is the process of any of Aspects 1-42, wherein in the reacting step, a contact time of the vapor-phase reactants with the catalyst is from about 1 second to about 100 seconds.

Aspect 45 is the process of any of Aspects 1-42, wherein in the reacting step, a contact time of the vapor-phase reactants with the catalyst is from about 2 second to about 50 seconds.

Aspect 46 is the process of any of Aspects 1-42, wherein in the reacting step, a contact time of the vapor-phase reactants with the catalyst is from about 10 second to about 30 seconds.

Aspect 47 is the process of any of Aspects 1-46, wherein the process further comprises the additional steps of separating unreacted iodine from the trifluoroiodomethane and returning the unreacted iodine to the providing step.

Aspect 48 is the process of any of Aspects 1-47, wherein the process is a continuous process.

Aspect 49 is the process of any of Aspects 1-47, wherein the process is a batch process.

Aspect 51 is the process of any of Aspects 1-49, wherein the trifluoroacetyl halide is selected from the group consisting of trifluoroacetyl fluoride, trifluoroacetyl chloride, trifluoroacetyl bromide, and any combinations thereof.

Aspect 52 is the process of any of Aspects 1-49, wherein the trifluoroacetyl halide comprises trifluoroacetyl chloride.

Aspect 53 is the process of any of Aspects 1-49, wherein the trifluoroacetyl halide consists essentially of trifluoroacetyl chloride.

Aspect 54 is the process of any of Aspects 1-49, wherein the trifluoroacetyl halide consists of trifluoroacetyl chloride.

Aspect 55 is a process for producing trifluoroiodomethane ($CF_3I$), the process including the following steps: reacting a trifluoroacetyl halide, hydrogen, and iodine in the vapor phase a temperature from about 200° C. to about 600° C. in the presence of a catalyst to produce a product stream comprising the trifluoroiodomethane, unreacted trifluoroacetyl halide, unreacted hydrogen, unreacted iodine, and hydrogen iodide, the catalyst comprising a transition metal; removing at least some of the unreacted iodine from the product stream by cooling the product stream to condense iodine from the vapor phase; and recycling the condensed iodine to the reacting step.

Aspect 56 is the process of Aspect 55, wherein the trifluoroacetyl halide comprises less than about 500 ppm by weight of water.

Aspect 57 is the process of Aspect 55, wherein the trifluoroacetyl halide comprises less than about 100 ppm by weight of water.

Aspect 58 is the process of Aspect 55, wherein the trifluoroacetyl halide comprises less than about 30 ppm by weight of water.

Aspect 59 is the process of Aspect 55, wherein the trifluoroacetyl halide comprises less than about 10 ppm by weight of water.

Aspect 60 is the process of any of Aspects 55-59, wherein the hydrogen comprises less than about 500 ppm by weight of water.

Aspect 61 is the process of any of Aspects 55-59, wherein the hydrogen comprises less than about 100 ppm by weight of water.

Aspect 62 is the process of any of Aspects 55-59, wherein the hydrogen comprises less than about 30 ppm by weight of water.

Aspect 63 is the process of any of Aspects 55-59, wherein the hydrogen comprises less than about 10 ppm by weight of water.

Aspect 64 is the process of any of Aspects 55-63, wherein the iodine comprises less than about 500 ppm by weight of water.

Aspect 65 is the process of any of Aspects 55-63, wherein the iodine comprises less than about 100 ppm by weight of water.

Aspect 66 is the process of any of Aspects 55-63, wherein the iodine comprises less than about 30 ppm by weight of water.

Aspect 67 is the process of any of Aspects 55-63, wherein the iodine comprises less than about 10 ppm by weight of water.

Aspect 68 is the process of any of Aspects 55-67, wherein a molar ratio of the hydrogen to the iodine is from about 0.1:1 to about 5:1.

Aspect 69 is the process of any of Aspects 55-67, wherein a molar ratio of the hydrogen to the iodine is from about 0.1:1 to about 1:1.

Aspect 70 is the process of any of Aspects 55-67, wherein a molar ratio of the hydrogen to the iodine is from about 0.3:1 to about 0.8:1.

Aspect 71 is the process of any of Aspects 55-67, wherein a molar ratio of the hydrogen to the iodine is from about 0.5:1 to about 0.7:1.

Aspect 72 is the process of any of Aspects 55-71, wherein a molar ratio of the hydrogen to trifluoroacetyl halide is from about 0.002:1 to about 1:1.

Aspect 73 is the process of any of Aspects 55-71, wherein a molar ratio of the hydrogen to trifluoroacetyl halide is from about 0.01:1 to about 0.05:1.

Aspect 74 is the process of any of Aspects 55-73, wherein the vapor-phase reactants comprise less than about 500 ppm by weight of oxygen.

Aspect 75 is the process of any of Aspects 55-73, wherein the vapor-phase reactants comprise less than about 100 ppm by weight of oxygen.

Aspect 76 is the process of any of Aspects 55-73, wherein the vapor-phase reactants comprise less than about 10 ppm by weight of oxygen.

Aspect 77 is the process of any of Aspects 55-73, wherein the vapor-phase reactants comprise less than about 3 ppm by weight of oxygen.

Aspect 78 is the process of any of Aspects 55-77, wherein the transition metal includes at least one selected from the group of nickel, cobalt, iron, rhodium, iridium, platinum, and palladium.

Aspect 79 is the process of any of Aspects 55-77, wherein the transition metal consists essentially of nickel, platinum, palladium, or combinations thereof.

Aspect 80 is the process of any of Aspects 55-77, wherein the transition metal consists essentially of nickel, platinum, palladium, or combinations thereof.

Aspect 81 is the process of any of Aspects 55-77, wherein the transition metal consists essentially of palladium.

Aspect 82 is the process of any of Aspects 55-81, wherein the catalyst further comprises a support including at least one selected from the group of an aluminum oxide support, a carbon support, a silica gel support, and a silicon carbide support.

Aspect 83 is the process of any of Aspects 55-81, wherein the catalyst further comprises a support consisting essentially of an aluminum oxide support.

Aspect 84 is the process of either of Aspects 82 or 83, wherein an amount of transition metal on the surface of the catalyst is from about 0.01 wt. % to about 40 wt. % of the total weight of the transition metal and the support.

Aspect 85 is the process of Aspect 84, wherein the transition metal includes at least one selected from the group of nickel, cobalt, iron, or combinations thereof, and the amount of transition metal on the surface of the catalyst is from about 5 wt. % to about 35 wt. % of the total weight of the transition metal and the support.

Aspect 86 is the process of Aspect 84, wherein the transition metal includes at least one selected from the group of nickel, cobalt, iron, or combinations thereof, and the amount of transition metal on the surface of the catalyst is from about 10 wt. % to about 30 wt. % of the total weight of the transition metal and the support.

Aspect 87 is the process of Aspect 84, wherein the transition metal includes at least one selected from the group of nickel, cobalt, iron, or combinations thereof, and the amount of transition metal on the surface of the catalyst is from about 20 wt. % to about 30 wt. % of the total weight of the transition metal and the support.

Aspect 88 is the process of Aspect 84, wherein the transition metal includes nickel, the support includes aluminum oxide, and the nickel is about 21 wt. % the total weight of the nickel and the aluminum oxide.

Aspect 89 is the process of Aspect 84, wherein the transition metal includes at least one selected from the group of rhodium, iridium, platinum, palladium, or combinations thereof, and the amount of transition metal on the surface of the catalyst is from about 0.1 wt. % to about 5 wt. % of the total weight of the transition metal and the support.

Aspect 90 is the process of Aspect 84, wherein the transition metal includes at least one selected from the group of rhodium, iridium, platinum, palladium, or combinations thereof, and the amount of transition metal on the surface of the catalyst is from about 0.3 wt. % to about 1 wt. % of the total weight of the transition metal and the support.

Aspect 91 is the process of Aspect 84, wherein the transition metal includes at least one selected from the group of rhodium, iridium, platinum, palladium, or combinations thereof, and the amount of transition metal on the surface of the catalyst is from about 0.3 wt. % to about 0.7 wt. % of the total weight of the transition metal and the support.

Aspect 92 is the process of Aspect 84, wherein the transition metal includes palladium, the support includes aluminum oxide, and the palladium is about 0.5 wt. % the total weight of the palladium and the aluminum oxide.

Aspect 93 is the process of any of Aspects 55-92, wherein the vapor-phase reactants are heated to a temperature from about 300° C. to about 400° C.

Aspect 94 is the process of any of Aspects 55-92, wherein the vapor-phase reactants are heated to a temperature from about 320° C. to about 360° C.

Aspect 95 is the process of any of Aspects 55-92, wherein the vapor-phase reactants are heated to a temperature from about 340° C. to about 360° C.

Aspect 96 is the process of any of Aspects 55-95, wherein in the reacting step, a contact time of the vapor-phase reactants with the catalyst is from about 0.1 second to about 1,200 seconds.

Aspect 97 is the process of any of Aspects 55-95, wherein in the reacting step, a contact time of the vapor-phase reactants with the catalyst is from about 1 second to about 100 seconds.

Aspect 98 is the process of any of Aspects 55-95, wherein in the reacting step, a contact time of the vapor-phase reactants with the catalyst is from about 2 second to about 50 seconds.

Aspect 99 is the process of any of Aspects 55-95, wherein in the reacting step, a contact time of the vapor-phase reactants with the catalyst is from about 10 second to about 30 seconds.

Aspect 100 is the process of any of Aspects 55-99, wherein the process further comprises the additional steps of separating unreacted trifluoroacetyl halide from the product stream; and recycling the separated trifluoroacetyl halide to the reacting step.

Aspect 101 is the process of any of Aspects 55-100, wherein the process further comprises the additional steps of separating unreacted hydrogen iodide from the product stream; and recycling the separated hydrogen iodide to the reacting step.

Aspect 102 is the process of any of Aspects 55-101, wherein the process is a continuous process.

Aspect 103 is the process of any of Aspects 55-101, wherein the process is a batch process.

Aspect 104 is the process of any of Aspects 55-103, wherein the trifluoroacetyl halide is selected from the group consisting of trifluoroacetyl fluoride, trifluoroacetyl chloride, trifluoroacetyl bromide, and any combinations thereof.

Aspect 105 is the process of any of Aspects 55-103, wherein the trifluoroacetyl halide comprises trifluoroacetyl chloride.

Aspect 106 is the process of any of Aspects 55-103, wherein the trifluoroacetyl halide consists essentially of trifluoroacetyl chloride.

Aspect 107 is the process of any of Aspects 55-103, wherein the trifluoroacetyl halide consists of trifluoroacetyl chloride.

What is claimed is:

1. A process for producing trifluoroiodomethane (CF3I), the process comprising:
   providing vapor-phase reactants comprising trifluoroacetyl halide, hydrogen, and iodine;
   heating the vapor-phase reactants; and
   reacting the heated vapor-phase reactants in the presence of a catalyst to produce trifluoroiodomethane, the catalyst comprising a transition metal.

2. The process of claim 1, wherein in the providing step, the trifluoroacetyl halide, the iodine, and the hydrogen each comprise less than about 500 ppm by weight of water.

3. The process of claim 1, wherein in the providing step, a molar ratio of the hydrogen to the iodine is from about 0.1:1 to about 0.9:1.

4. The process of claim 1, wherein in the providing step, a molar ratio of the hydrogen to the trifluoroacetyl halide is from about 0.01:1 to about 0.05:1.

5. The process of claim 1, wherein the transition metal includes at least one selected from the group of nickel, cobalt, iron, rhodium, iridium, platinum, and palladium.

6. The process of claim 5, wherein the catalyst further comprises a support including at least one selected from the group of an aluminum oxide support, a carbon support, a silica gel support, and a silicon carbide support.

7. The process of claim 6, wherein the transition metal is from about 0.01 wt. % to about 40 wt. % of the total weight of the transition metal and the support.

8. The process of claim 7, wherein the transition metal includes palladium, the support includes aluminum oxide, and the palladium is about 0.5 wt. % of the total weight of the palladium and the aluminum oxide.

9. The process of claim 7, wherein the transition metal includes nickel, the support includes aluminum oxide, and the nickel is about 21 wt. % of the total weight of the nickel and the aluminum oxide.

10. The process of claim 1, wherein the vapor-phase reactants are heated to a temperature from about 200° C. to about 600° C.

11. The process of claim 1, wherein the trifluoroacetyl halide comprises trifluoroacetyl chloride.

12. The process of claim 1, wherein the process further comprises the additional steps of:
   separating unreacted iodine from the trifluoroiodomethane; and
   returning the unreacted iodine to the providing step.

13. The process of claim 1, wherein the process is a continuous process.

14. The process of claim 1, wherein the process is a batch process.

15. A process for producing trifluoroiodomethane (CF3I), the process comprising the following steps:
   reacting a trifluoroacetyl halide, hydrogen, and iodine in the vapor phase a temperature from about 200° C. to about 600° C. in the presence of a catalyst to produce a product stream comprising the trifluoroiodomethane, unreacted trifluoroacetyl halide, unreacted hydrogen, unreacted iodine, and hydrogen iodide, the catalyst comprising a transition metal;
   removing at least some of the unreacted iodine from the product stream by cooling the product stream to condense iodine from the vapor phase; and
   recycling the condensed iodine to the reacting step.

16. The process of claim 15, wherein a molar ratio of the hydrogen to the iodine is from about 0.1:1 to about 0.9:1.

17. The process of claim 15, wherein the transition metal includes at least one selected from the group of nickel, cobalt, iron, rhodium, iridium, platinum, and palladium.

18. The process of claim 17, wherein the catalyst further comprises a support including at least one selected from the group of an aluminum oxide support and a carbon support, and the transition metal is from about 0.01 wt. % to about 40 wt. % of the total weight of the transition metal and the support.

19. The process of claim 15, wherein a molar ratio of the hydrogen to the trifluoroacetyl halide is from about 0.01:1 to about 0.05:1.

20. The process of claim 15, wherein the process further comprises the additional steps of:
  separating the unreacted trifluoroacetyl halide from the product stream; and
  recycling the separated trifluoroacetyl halide to the reacting step.

* * * * *